(12) United States Patent
Horino

(10) Patent No.: US 7,682,622 B2
(45) Date of Patent: *Mar. 23, 2010

(54) COSMETICS

(75) Inventor: Masaakira Horino, Kanagawa (JP)

(73) Assignee: Miyoshi Kasei, Inc., Saitama-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/069,904

(22) Filed: Mar. 2, 2005

(65) Prior Publication Data

US 2005/0196363 A1    Sep. 8, 2005

(30) Foreign Application Priority Data

Mar. 2, 2004    (JP) ............................. 2004-057674

(51) Int. Cl.
*A61K 8/02* (2006.01)
*C08F 283/12* (2006.01)
*C08G 77/00* (2006.01)

(52) U.S. Cl. ................... 424/401; 525/477; 525/478

(58) Field of Classification Search ............. 424/70.121
See application file for complete search history.

(56) References Cited

U.S. PATENT DOCUMENTS

| | | | | | |
|---|---|---|---|---|---|
| 4,477,375 | A | * | 10/1984 | Grollier | 424/70.19 |
| 4,710,374 | A | * | 12/1987 | Grollier et al. | 424/61 |
| 4,871,616 | A | | 10/1989 | Kimura et al. | |
| 4,892,726 | A | * | 1/1990 | Yonekura et al. | 424/63 |
| 4,912,056 | A | * | 3/1990 | Olson | 435/263 |
| 5,034,476 | A | * | 7/1991 | Saito et al. | 525/477 |
| 5,075,102 | A | * | 12/1991 | Hubaud et al. | 424/59 |
| 5,106,922 | A | * | 4/1992 | Saito et al. | 525/477 |
| 5,264,207 | A | * | 11/1993 | Bommelaer et al. | 424/69 |
| 5,580,549 | A | * | 12/1996 | Fukuda et al. | 424/62 |
| 5,783,601 | A | * | 7/1998 | Tanahashi et al. | 514/557 |
| 6,083,491 | A | * | 7/2000 | Mellul et al. | 424/63 |
| 6,106,847 | A | * | 8/2000 | Ferrero et al. | 424/401 |
| 2004/0057920 | A1 | * | 3/2004 | Focht et al. | 424/70.1 |
| 2004/0126401 | A1 | * | 7/2004 | Collin | 424/401 |

FOREIGN PATENT DOCUMENTS

| | | | |
|---|---|---|---|
| JP | 5-25019 | | 2/1993 |
| JP | 9-104833 | | 4/1997 |
| JP | 10036232 | A * | 2/1998 |
| JP | 10-139624 | | 5/1998 |
| JP | 10-175816 | | 6/1998 |
| JP | 2002-235004 | | 8/2002 |

OTHER PUBLICATIONS

GE Bayer Silicones (Tospearl series).*

* cited by examiner

*Primary Examiner*—Sreeni Padmanabhan
*Assistant Examiner*—Layla Soroush
(74) *Attorney, Agent, or Firm*—Westerman, Hattori, Daniels & Adrian, LLP

(57) ABSTRACT

A surface of particles of a silicone resin is treated with a low-molecular organosilicon derivative, with or without a water-soluble cationic polymer to improve the hydrophilicity of the silicone resin. The thus-treated powder is quite excellent in dispersibility (readily dispersible) and in dispersion stability in an aqueous dispersion medium. The use of the surface-treated powder provides a dispersion for cosmetic, excellent in dispersibility and dispersion stability and the like. The use of the surface-treated powder, or the use of the dispersion provides further a cosmetic excellent in dispersibility and dispersion stability, and further excellent in ease of re-dispersion and dispersion stability with lapse of time when selecting aqueous cosmetic as an agent form, and also excellent in smooth feeling in comparison with ordinary products.

9 Claims, No Drawings

COSMETICS

FIELD OF THE INVENTION

The present invention relates to a novel surface-treated powder for a cosmetic in which a surface of particles of a silicone resin (powder), for example, diorganosiloxane, organosilsesquioxane and the like, especially polymethylsilsesquioxane, is treated (coated) with a low-molecular organosilicon derivative, with or without a water-soluble cationic polymer, and to a dispersion for a cosmetic and cosmetics containing the same.

According to the present invention, it is possible to suppress agglomeration (aggregation) of a powder (silicone resin) to be incorporated (blended) in an aqueous dispersion medium (dispersion medium (dispersant) of aqueous type) or cosmetics, while it is also possible to disperse the powder uniformly in the aqueous dispersion medium or the cosmetics and further to maintain the dispersed state for a long period of time. Such cosmetics are quite excellent in smooth (application) feeling such as moist (dewy) touch.

BACKGROUND OF THE INVENTION

Cosmetics contain powders or pigments for improving coloration, feeling and the like. When powders or pigments are used for these purposes, it is required to uniformly disperse the powders or the pigments in cosmetics (cosmetic compositions) to obtain cosmetics having high dispersion stability without unevenness in color and the like. However, when ordinary powders or pigments are selected and dispersed in an aqueous dispersion medium, there is a need to hydrophilize (make a hydrophilic treatment) them for homogenizing property of the surface thereof. Without hydrophilization (hydrophilic-treatment), it is impossible to obtain cosmetics having good dispersibility and dispersion stability (dispersion stability with lapse of time).

Meanwhile, many proposals have been so far made for hydrophilicaly treating hydrophobic powders or pigments. Methods for mixing a hydrophilized (hydrophilicaly treated) silicone resin which is obtained by hydrophilizing (hydrophilicaly treating) a silicone resin having heat resistance, weather ability (weather resistance), electric insulating property, chemical resistance, water resistance, and the like as a powder in cosmetics have been studied (refer to Japanese Patent Kokai Publication JP-A-10-139624, Japanese Patent Kokai Publication JP-A-10-175816, Japanese Patent Kokai Publication JP-A-2002-235004 and Japanese Patent Kokai Publication JP-A-9-104833).

For example, it is proposed that the silicone resin is hydrophilicaly treated with surfactant such as nonionic surfactant, anionic surfactant, cationic surfactant, ampholytic surfactant or these mixture to disperse the silicone resin in an aqueous dispersion medium, and it is reported that a cosmetic (cosmetic of aqueous type) containing the dispersion which is obtained by dispersing the treated powder thus obtained into an aqueous dispersion medium can be improved in smooth feeling (refer to Japanese Patent Kokai Publication JP-A-10-139624, Japanese Patent Kokai Publication JP-A-10-175816 and Japanese Patent Kokai Publication JP-A-2002-235004).

However, since the silicone resin described above has an extremely strong water-repellent property (hydrophobic property), the method of hydrophilic treatment (surface treatment) with the above surfactant or a water-soluble polymer is said to be hard in being satisfactory for dispersing such powder (silicone resin) in an aqueous dispersion medium. When the hydrophilicaly treated (hydrophilicaly-treated) powder is incorporated into cosmetics therewith, the powder(s) or the pigment(s) is dissociated or separated in the system, and subsequently aggregates. Consequently, this causes uneven color or a difference between color in appearance (appearance color) and color at the time of application (application color) therein or dispersion stability with lapse of time is impaired, or in case of some form of cosmetics, the re-dispersibility of the powders or the pigments in the system may be worsened to cause caking and notably decreases its usability.

It is however quite difficult to disperse the above silicone resin (particles) in an aqueous dispersion medium by hitherto-proposed methods for hydrophilicaly treating hydrophobic powders or pigments.

For example, a hydrophilicaly surface treated pigment in which a hydrophilic organic group is introduced into a pigment using a hydrophilic silane compound or silane coupling agent and a composition containing the same are proposed (refer to Japanese Patent Kokai Publication JP-A-9-104833). However, the above-mentioned hydrophilicaly surface treated pigment (s) in which a hydrophilic organic group is introduced into a pigment using a hydrophilic silane compound or silane coupling agent aggregates in the system, and consequently an uneven color is caused or a conformity between color in appearance and color at the time of application worsens, so that dispersibility and dispersion stability is not satisfactory. Therefore, even when using a silicone resin having an extremely strong hydrophobic property, dispersibility and dispersion stability in the system of cosmetics is not satisfactory and furthermore impairs the effects of the silicone resin such as slip (lubricant property), extension (spreadability) on skin, and dry touch.

In makeup products containing powders, a cake type foundation for example, a humectant has been used to impart a moist feel for a smooth feeling, especially a smooth feeling after use on the skin. However, when cosmetics containing a humectant are applied on the skin, since the oil absorption or water absorption of the powder is too strong, the powder adsorbs the sebum or moisture, more than as required from the skin. That is, cosmetics containing a humectant lack a smooth feeling, especially a moist touch (feel), and the use of a humectant in cosmetics causes an increase in a rough feeling or a dry feeling of the skin. Accordingly, when such cosmetics are applied on the skin, it provides a hard feeling to skin, and not a soft feeling. In addition, affixture of a powder contained in cosmetics to the skin is worsened, and adhesion of a cosmetic film on the skin is deficient. Consequently, these defects also causes the makeup to come off. Especially, the rough feeling of the skin has been clearly problematic during the winter.

In order to solve this problem, the addition of a humectant such as glycerin, propylene glycol or 1,3-butylene glycol to cosmetics has been attempted so far. When cosmetics containing a powder are produced by simply mixing a humectant with other ingredients, various ingredients are used as starting materials for cosmetics to be adhered to or adsorbed on the surface of the powder, and further the surface properties of the powder become heterogeneous, and the affixture to the skin decreases. Consequently, the rough feeling and the dry feeling of the skin cannot be improved, and the makeup is liable to come off due to secretion from the skin, movement of muscles of facial expression, and the like. In addition, when the humectant is incorporated (mixed) along with the powder, the low-molecular part of the humectant is adsorbed on the powder, but the majority of the humectant is easily desorbed from the surface of the powder, so that a mere wetting phenomenon is shown. Thus, the humectant does not basically change the surface properties of the powder. Accordingly, it is impossible to decrease the rough feeling on the skin caused by the powder and improve the affixture to the skin, so that the moist touch cannot be improved and maintained. Moreover, the unevenness of the cosmetic film caused by the powder formed on the skin cannot basically be eliminated, thereby contributing to the makeup coming off the skin.

There is also a method in which affinity for water in a powder is increased by treating the powder with silica and alumina. However this method has been problematic in that the surface activity of the powder does not have sufficient dispersibility in water. Furthermore, in cosmetics containing the treated powder (silica/alumina-treated powder), the powder itself and the surface-treating agent applied to its surface become separated or dissociated. Consequently, the powder aggregates in the system, or thereby a difference between the appearance color and application color is caused. In addition, depending on the different form of cosmetics, for example, in case of a cosmetic of bi-layer type, the powder might cause a caking phenomenon to notably decrease re-dispersibility and greatly impair usability.

Accordingly, in a system in which the cosmetics (especially cosmetics of aqueous type) contain a hydrophilicaly treated powder (surface-treated powder) prepared by hydrophilicaly treating a silicone resin (particles) by the above conventional hydrophilicaly treating method of hydrophilic treatment, the particles of the silicone resin aggregate, or the dispersion stability with lapse of time is impaired. Thus, the effects thereof are hard to exhibit satisfactorily. Therefore, it is desirable to develop a powder for cosmetics obtained by hydrophilicaly treating the silicone resin (particles). Additionally, no description has been found with respect to a surface-treated powder which is prepared by hydrophilicaly treating the silicone resin (particles) which is excellent in dispersibility and dispersion stability, a dispersion and cosmetics containing the same, and the like.

SUMMARY OF THE INVENTION

Under these circumstances, it is an object of the present invention to provide a powder, in the concrete, a powder of a silicone resin, which has satisfactory hydrophilic property and is excellent in dispersibility (ease of dispersion) in an aqueous dispersion medium, and dispersion stability (stability with lapse of time), a dispersion for cosmetics which contains the same and is excellent in dispersibility and dispersion stability, and a cosmetic which contains the same and is excellent in dispersibility, dispersion stability and smooth feeling, especially moist touch, also excellent in perseverance of such a smooth feeling and further excellent in ease of re-dispersion (readily re-dispersible) and dispersion stability with lapse of time in case of selecting an aqueous cosmetic (cosmetic of aqueous type) as an agent form.

As a result of perseverant researches towards the hydrophilic treatment of silicone resin (particles), the present inventors have found that, in a surface-treated powder (hydrophilicaly treated silicone resin) obtained by surface-treating (coating) a silicone using low-molecular organosilicon derivatives, the powder is uniformly dispersed in the aqueous dispersion medium or the cosmetics and further the dispersed state is maintained for a long period of time, that is, the dispersibility (ease of dispersion) in the aqueous dispersion medium and the dispersion stability (dispersion stability with lapse of time) are excellent, and especially that a surface-treated powder obtained by surface-treating a silicone resin using low-molecular organosilicon derivatives and a water-soluble cationic polymer is superior in dispersibility in the aqueous dispersion medium and the dispersion stability. It has been further found that when such a powder is incorporated in an aqueous dispersion medium, the dispersion becomes quite excellent in dispersibility and dispersion stability, which can be produced, owing to the dispersibility and the dispersion stability of the powder. Cosmetics, containing the surface-treated powder or the dispersion containing the same, are excellent in dispersibility and dispersion stability and further excellent in ease of re-dispersion and dispersion stability with lapse of time in case of selecting aqueous cosmetics as the agent form thereof, impart an excellent smooth feeling, especially a moist touch to the skin and are also excellent in perseverance thereof. These findings have led to the completion of the present invention.

That is, the present invention lies in a surface-treated powder (hereinafter also referred to as "the surface-treated powder of the present invention"), preferably a surface-treated powder for cosmetics, in which a powder to be surface-treated is a silicone resin, and the surface of particles of said silicone resin is coated with a low-molecular organosilicon derivative, with or without a water-soluble cationic polymer.

In the present invention, polymethylsilsesquioxane can be selected as said silicone resin, at least one of dimethylsilanediol hyaluronate, monomethylsilanetriol lactate, and methylsilanol-tri-PEG-8-glyceryl cocoate can be selected as said low-molecular organosilicon derivative, and at least one of a dimethyldiallylammonium chloride-acrylamide copolymer, polydimethylmethylenepiperidinium chloride and o-[2-hydroxy-3-(trimethylammonio)propyl]hydroxyethylcellulose chloride can be selected as said water-soluble cationic polymer.

In the present invention, the particle size of particles of said silicone resin can be from 0.1 to 100 μm in terms of a mean particle size.

The surface of particles of said silicone resin can be coated with said low-molecular organosilicon derivative, with or without said water-soluble cationic polymer from 0.1 to 50% by weight, based on the surface of particles of said silicone resin.

In another embodiment, the present invention lies in a dispersion for a cosmetic (hereinafter also referred to as "the dispersion of the present invention") which comprises the surface-treated powder described above.

In still another embodiment, the present invention lies in a cosmetic (hereinafter also referred to as "the cosmetic of the present invention") which comprises the surface-treated powder described above.

It is preferable to use the cosmetic of the present invention in a cosmetic of a bi-layer type, a three-layer type, a water-in-oil (W/o) emulsion type, an oil-in-water (O/W) emulsion type, a gel type, a spray type, a mousse type, oil type, solid type or a stick type, especially as a jelly pack, a gel foundation, a suncum lotion or an emulsion.

The meritorious effects of the present invention are summarized as follows.

The present invention can provide a surface-treated powder, which is easily dispersed uniformly in an aqueous dispersion medium. The present invention can also provide a dispersion containing (dispersing) said surface-treated powder, with excellent dispersibility (ease of dispersion) and dispersion stability.

Further, using said surface-treated powder or said dispersion, a cosmetic with excellent dispersibility and dispersion stability and further, in case of selecting aqueous cosmetic, excellent ease of re-dispersion and dispersion stability with lapse of time and superior in smooth feeling such as moist touch and the like can be produced easily and simply. Therefore, the present invention is especially useful in a cosmetic industry.

PREFERRED EMBODIMENTS OF THE INVENTION

A surface-treated powder prepared by coating the surface of a silicone resin (particles) with a low-molecular organosilicon derivative, with or without a water-soluble cationic polymer, namely, the surface-treated powder of the present invention and the dispersion containing the same are described in detail as below. However, the present invention is not limited thereto. Incidentally, in the present invention, "silicone resin" may be in the form of either a powder or particles.

(Surface-Treated Powder of the Invention)

The surface-treated powder of the present invention is a surface-treated powder for a cosmetic(s). The powder to be surface-treated is a silicone resin, and the surface of particles of the silicone resin is coated with a low-molecular organosilicon derivative, with or without a water-soluble cationic polymer.

The powder (powder before being surface-treated) used in the present invention is a silicone resin.

There is no limitation to the silicone resin described above. For example, a silicone resin consisting of a combination of bifunctional silicone resin and trifunctional silicone resin, or a trifunctional silicone resin, or the like can be used. Preferably, a trifunctional silicone resin such as polymethylsilsesquioxane, especially preferably, polymethylsilsesquioxane is selected. The silicone resin described above is easily available. Silicone resins produced by a known method or purchased from a market (for example, trade name: TOSPEARL, manufactured by GE Toshiba Silicones, Ltd.) can be used.

In the present invention, a low-molecular organosilicon derivative(s) is used. As a low-molecular organosilicon derivative used in the present invention, silanols having a polysiloxane molecule of an oligomer, containing some silicon-carbon (Si—C) bonds, silicon-hydroxy bonds (Si—OH) or Si—O—C bonds and having an alkylsilanol structure such as a methylsilanol or dimethylsilanol structure are selected which have high safety and high moisture retention and are quite excellent in activity of repairing and regenerating tissue and their affinity for the skin.

The low-molecular organosilicon derivative is generally represented by the following formula (1), is soluble in water and has biological activity.

$$X[R_nSi(OH)_{4-n}] \quad (1)$$

wherein 0<n<4, X>4, and R represents an alkyl group.

Examples of the low-molecular organosilicon derivative(s) include monomethylsilanetriol mannuronate ($CH_3$—Si($OH$)$_2$—O—$C_6H_9O_6$), dimethylsilanediol hyaluronate ($CH_3$—Si($OR$)$_2$ in which R represents a hyaluronyl group), a mixture of silanol cafeate and silanol mannuronate, elastin peptide silane ($CH_3$—Si($OH$)$_2$OR in which R represents an elastin polypeptide), monomethylsilanetriol lactate ($CH_3$—Si($OH$)$_2$—O—$C_3H_5O_2$), trioleyloxymonomethylsilane ($C_{56}H_{22}SiO_3$), methylsilanol-tri-PEG-8-glyceryl cocoate  ($CH_3$—Si($OC_2H_4OR$)$_3$ in which R represents a coconut oil fatty acid glyceryl), methylsilanol alginate ester, dimethylsilanediol-butylene glycol-triethanolamine, a dimethylsilanol-hyaluronic acid condensate, silanediol salicylate, a methylsilanol-lactic acid condensate, an aspartic acid-monohydroxyprolinemonomethylsilanol salt solution, a methylsilanol-hydrolyzed elastin condensate, dimethyloxobenzodioxasilane and the like. At least one of dimethylsilanediol hyaluronate, monomethylsilanetriol lactate and methylsilanol-tri-PEG-8-glyceryl cocoate is preferably selected.

Examples of the water-soluble cationic polymer(s) used in the present invention include chitin derivatives such as chitosan, partially hydrolyzed chitin, chitosan-dl-pyrrolidonecarboxylate, succinylchitosan and hydroxypropylchitosan, dimethyldiallylammonium chloride derivatives such as a dimethyldiallylammonium chloride-acrylamide copolymer and polydimethylmethylenepiperidinium chloride, cationized celluloses such as o-[2-hydroxy-3-(trimethylammonio)propyl]hydroxyethylcellulose chloride and o-[2-hydroxy-3-(lauryldimethylammonio)propyl]hydroxycellulose chloride, quaternary nitrogen-modified polysaccharides such as cationized modified cellulose and cationized locust bean gum, cationized guar gums such as o-[2-hydroxy-3-(trimethylammonio)propyl chloride guar gum, methacrylic acid derivatives such as a methacryloylethyldimethylbetaine-methacryloylethyltrimethy lammonium chloride-methoxypolyethylene glycol methacrylate copolymer, a methacryloylethyldimethylbetaine-methacryloylethyltrimethy lammonium chloride-2-hydroxyethyl methacrylate copolymer and a vinylpyrrolidone-N,N-dimethylaminoethyl methacrylate copolymer diethyl sulfate, vinylpyrrolidone derivatives such as a vinylpyrrolidone-dimethylaminoethyl methacrylate copolymer, a vinylpyrrolidone-methacrylamidopropyltrimethylammonium chloride copolymer and a vinylpyrrolidone-methylvinylimidazolium chloride copolymer, a dimethylallylammonium chloride-acrylamide copolymer containing diallyldimethylammonium chloride being a quaternary cationic monomer as a constituent, an acrylamide-acrylic acid-dimethyldiallylammonium chloride copolymer, polydimethylmethylenepiperidinium chloride, cathionized tamarind and the like. However, they are not limited thereto. At least one of a dimethyldiallylammonium chloride-acrylamide copolymer, polydimethylmethylenepiperidinium chloride and o-[2-hydroxy-3-(trimethylammonio)propyl]hydroxyethylcellulose chloride is preferably selected.

The foregoing surface-treating (surface treatment) substance (the low-molecular organosilicon derivative, or the low-molecular organosilicon derivative and the water-soluble cationic polymer) used in the present invention is adsorbed and coated on the surface of particles of the silicone resin to thereby change the water absorption property (water absorption amount) or oil absorption property (oil absorption amount) inherent in the silicone resin, to provide effects of inhibiting a rough feeling of the skin which could not be removed with ordinary powders and causing the makeup to come off through improvement of adhesion to the skin, and also to attain novel organolepticproperties (sensory characteristics) (elasticity and tonicity of the skin in the long-term and continuous use, and the like), stable ease of re-dispersion over an extended time period (with long-term lapse of time) in an aqueous system and stability over an extended time period for cosmetics (cosmetic compositions).

The mean particle size of the silicone resin which is used in the present invention (uncoated powder) is in the range from 0.1 to 500 μm or so, preferably from 0.1 to 100 μm or so, more preferably from 0.1 to 50 μm or so, especially preferably from 0.5 to 50 μm or so. When the mean particle size is less than the lower limit of the foregoing range, the silicone resin is difficult to prepare. Meanwhile, with respect to the silicone resin in which the mean particle size exceeds the upper limit of the foregoing range, cosmetics (compositions) obtained by using the same, give a rough feeling (touch) to impart an uncomfortable feeling to the skin, and in addition seem likely to decrease ease of re-dispersion or stability over an extended time period of cosmetics (compositions). With regard to the form (shape) of the particles of this silicone resin, aspherical, flat, indefinite (amorphous), and biconvex (spindle-like) form are cited. The preferable form of the particles is a spherical form.

In the present invention, the silicone resin described above can be surface-treated (coated) with the above low-molecular organosilicon derivative alone or the above low-molecular organosilicon derivative in combination with the above water-soluble cationic polymer. When the above low-molecular organosilicon derivative is used in combination with the above water-soluble cationic polymer, it is possible that the above low-molecular organosilicon derivative and the above water-soluble cationic polymer are simultaneously surface-treated to the silicone resin, or that following one of the surface-treating substances, the above low-molecular organosilicon derivative and the above water-soluble cationic polymer, the other one is surface-treated.

In the hydrophilic surface treatment using the above low-molecular organosilicon derivative alone or the above low-molecular organosilicon derivative in combination with the above water-soluble cationic polymer, the surface of particle(s) of the silicone resin is hydrophilicaly treated by being directly treated with the surface-treating substance. In this treatment, for example, a method is employed which comprises a step of adding the low-molecular organosilicon derivative, the water-soluble cationic polymer and the particles of the silicone resin described above to water or, as required, a mixed solution of water and alcohol, stirring or ball-milling the resulting mixture, subsequently repeating water-washing and filtration thereof, to remove contaminants, and subsequently drying and pulverizing the product obtained. For the method(s) itself, any known method can be employed.

The amount of the above surface-treating substance (hydrophilicaly treating agent) treated on the surface of the above silicone resin (particles) can be selected depending on the form and the mean particle size of particles of the silicone resin used, and it is not particularly limited. It is preferably from 0.1 to 50% by weight or so, more preferably from 0.3 to 40% by weight or so, further preferably from 1.0 to 30% by weight or so based on the silicone resin (to be surface-treated) before the surface treatment.

In the surface-treated powder of the present invention, the low-molecular organosilicon derivative, or the low-molecular organosilicon derivative and the cationic water-soluble polymer are firmly adsorbed on the surface of the silicone resin. Further, a part thereof is bonded with and coats the surface of particles of the silicone resin. Thus, the surface-treated powder is easy to re-disperse in an aqueous system, excellent instability with lapse of time, has long-term storage stability in cosmetic compositions, has an ability of inhibiting (preventing) a rough feeling on the skin caused by resin powder, and has the ability of preventing the makeup from coming off due to excellent affixture to the skin. Furthermore the surface-treated powder of the present invention can be incorporated as a powder in water dispersion or cosmetics in the same manner for incorporating ordinary powders or pigments therein.

(Dispersion of the Invention)

The dispersion of the present invention contains the surface-treated powder described above (the surface-treated powder of the present invention). The surface-treated powder of the present invention can be prepared in the foregoing manner. Moreover, the surface-treated powder is uniformly dispersed in the aqueous dispersion medium such as water, stably over the course of time. Especially, it is quite excellent in dispersibility and dispersion stability as a dispersion for a cosmetic(s).

In the dispersion of the present invention, one or more kinds of the surface-treated powders described above can be contained in the aqueous dispersion medium, and such a dispersion is also included in the dispersion of the present invention.

The aqueous dispersion medium is not particularly limited, and water is therefore usually selected.

In the present invention, the surface-treated powder described above can be mixed with and dispersed in the aqueous dispersion medium by a known method, and the method is not particularly limited. For example, the dispersion can be produced using a wet mixing/dispersing machine (equipment) such as a propeller mixer, a high-speed mixer, a dissolver (disperser), a homogenizer, a fluid-jet-mill, a colloid mill, a mass colloider (disk grinder), a bead mill or a sand mill.

In the composition of the dispersion of the present invention, the use amount of the surface-treated powder described above is not particularly limited. It is preferably from 0.1 to 70% by weight or so.

(Cosmetics of the Invention)

The cosmetics of the present invention are cosmetics containing the surface-treated powder described above (the surface-treated powder of the present invention) or the dispersion described above (the dispersion of the present invention). That is, the surface-treated powder and the dispersion can be prepared (produced) as described above.

In the present invention, the preparation (production) of the cosmetics is not particularly difficult, and the desired cosmetics can be obtained by any technique (for example, emulsification) which has been so far employed in using a surface-treated powder or dispersion for cosmetics.

When the surface-treated powder (hydrophilicaly treated silicone resin) of the present invention is contained in cosmetics (cosmetic compositions), the amount (mixed amount) thereof is not particularly limited. It is preferably from 0.1 to 99% by weight or so, more preferably from 0.1 to 95% by weight or so based on the total cosmetic composition. Further, when the dispersion of the present invention is contained in the cosmetics, its amount is not particularly limited.

The cosmetics of the present invention can further contain an ultraviolet light absorbing agent (absorber). Examples of an ultraviolet light absorber include cinnamic acid-based (type) ultraviolet light absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate, 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate and glyceryl mono-2-ethylhexanoyl-di-para-methoxycinnamate; benzophenone-based ultraviolet absorbers such as 2,4-dihydroxybenzophenone, 2,2'-dihydroxy-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone; para-aminobenzoic acid-based ultraviolet light absorbers such as PABA-monoglycerin ester, N,N-dipropoxy-PABA-ethyl ester, N,N-diethoxy-PABAethyl ester, N,N-dimethyl-PABA-ethyl ester, N,N-dimethyl-PABA-butyl ester and N,N-dimethyl-PABA-methyl ester; salicylic acid-based ultraviolet light absorbers such as aminosalicylate, menthyl salicylate, homomenthyl salicylate, octyl salicylate, phenyl salicylate, benzyl salicylate and p-isopropanolphenyl salicylate; anthranylic acid-based ultraviolet light absorbers such as methyl anthranylate; 3-(4'-methylbenzylidene)-d-camphor; 3-benzylidene-d,1-camphor; urocanic acid; ethyl urocanate (urocanic acid ethyl ester); octyltriazone; 2-phenyl-5-methylbenzoxazole; 2-(2'-hydroxy-5'-methylphenyl)benzotriazole; and 4-methoxy-4'-t-butylbenzoylmethane and the like. The amount (mixed amount) of these ultraviolet light absorbers is not particularly limited, and a high ultraviolet light preventive (protective) effect is obtained with a small amount thereof.

The cosmetics of the present invention can further contain, as required, other components routinely used for cosmetics unless the objects and effects (dispersibility, dispersion stability and the like) of the present invention are impaired. Examples thereof include liquid fats and oils, solid fats and oils, liquid or solid fats and oils, waxes, ester oils, hydrocarbon oils, silicones, lower alcohols, sterols, humectants, sequeatering agents, neutralizers, pH adjusting agents, antioxidants, antibacterial agents, various extracts, medicaments, and the like.

Examples of the above liquid fats and oils include linseed oil, camellia oil, macadamia nutoil, corn oil, mink oil, olive oil, avocado oil, sasanqua oil, castor oil, safflower oil, apricot kernel oil, cinnamon oil, jojoba oil, grape oil, sunflower oil, almond oil, rapeseed oil, sesame oil, wheat germ oil, rice germ oil, rice bran oil, cottonseed oil, soybean oil, peanut oil, tea seed oil, evening primrose oil, egg yolk oil, neatsfoot oil, liver oil, triglycerin, glycerin trioctanoate, glycerin triisopalmitate and the like.

Examples of the above solid fats and oils include cacao butter, beef tallow, mutton tallow, lard, horse fat, hardened oil, hardened castor oil, Japan wax, shea butter and the like.

Examples of the above liquid or solid fats and oils include coconut oil, palm oil, palm kernel oil and the like.

Examples of the above waxes include beeswax, candelilla wax, cotton wax, carnauba wax, bayberry wax, Chinese wax, spermacetiwax, montanwax, branwax, lanoline, reduced lanoline, hard lanoline, kapok wax, sugar cane wax, jojoba wax, shellac wax and the like.

Examples of the above ester oils include octanoates (octanoic acid esters) such as cetyl octanoate, isooctanoates (isooctanoic acid esters) such as glycerin tri-2-ethylhexanoate and pentaerythritol tetra-2-ethylhexanoate, laurates (lauric acid esters) such as hexyl laurate, myristates (miristic acid esters) such as isopropyl myristate and octyldodecyl myristate, palmitates (palmitic acid esters) such as octyl palmitate, stearates (stearic acid esters) such as isocetyl stearate, isostearates (isostearic acid esters) such as isopropyl isostearate, isopalmitates (isopalmitic acid esters) such as octyl isopalmitate, oleates (oleic acid esters) such as octyldodecyl oleate, adipic acid diesters such as diisopropyl adipate, sebacic acid diesters such as diethyl sebacate, diisostearyl maleate and the like.

Examples of the above hydrocarbon oils include liquid paraffin, ozocerite (ozokerite), squalane, squalene, pristane, paraffin, isoparaffin, ceresin, vaseline (petrolatum), microcrystalline wax and the like.

Examples of the above silicones include linear silicones such as dimethylpolysiloxane, methylphenylpolysiloxane and methylhydrogenpolysiloxane, and cyclic silicones such as octamethylcyclotetrasiloxane, decamethylcyclopentasiloxane and dodecamethylcyclohexasiloxane.

Examples of the above lower alcohols include methanol, ethanol, propanol, isopropanol and the like.

Examples of the above sterols include cholesterol, sitosterol, phytosterol, lanosterol and the like.

Examples of the above humectants include 1,2-pentanediol, 1,2-hexanediol, 1,2-heptanediol, polyethylene glycol, propylene glycol, dipropylene glycol, 1,3-butylene glycol, hexylene glycol, glycerin, diglycerin, sorbitol and the like.

Examples of the above sequestering agents include alanine, sodium edetate in the form of salt, sodium polyphosphate, sodium metaphosphate, phosphoric acid and the like.

Examples of the above neutralizers agents include 2-amino-2-methyl-1-propanol, 2-amino-2-methyl-1,3-propanediol, potassium hydroxide, sodium hydroxide, amino acids such as L-arginine and L-lysine, triethanolamine, sodium carbonate and the like.

Examples of the above pH adjusting agents include lactic acid, citric acid, glycolic acid, succinic acid, tartaric acid, dl-malic acid, potassium carbonate, sodium hydrogencarbonate, ammonium hydrogencarbonate and the like.

Examples of the above antioxidants include ascorbic acid, α-tocopherol, dibutylhydroxytoluene, butylhydroxyanisol and the like.

Examples of the above antibacterial agents include benzoic acid, salicylic acid, carbolic acid, sorbic acid, para-oxybenzoate, para-chloromethacresol, hexachlorophene, benzalkonium chloride, chlorhexidine chloride, trichlorocarbamide, sensitizing dyes, phenoxyethanol and the like.

Examples of the various extracts described above include saururaceae extract, phellodendron bark extract, melilot extract, dead nettle extract, glycyrrhiza extract, peony root extract, soapwort extract, gourd extract, cinchona extract, strawberry geranium extract, sophora extract, nuphar extract, fennel extract, primrose extract, rose extract, Rehmannia root extract, lemon extract, lithospernum root extract, aloe extract, calamus extract, eucalyptus extract, field horsetail extract, sage extract, thyme extract, tea extract, seaweed extract, cucumber extract, clove extract, brawble extract, melissa extract, ginseng extract, carrot extract, horse chestnut extract, peach extract, peach leaf extract, mulberry extract, crop weed extract, hamamerris liquid extract, placenta extract, thymus grand extract, silk liquid extract and the like.

Examples of the above medicaments include vitamins such as vitamin A oil, retinol, retinol palmitate, inositol, pyridoxine hydrochloride, benzyl nicotinate, nicotinic acid amide, DL-α-tocopherol nicotinate, ascorbic acid magnesium phosphate, vitamin D2 (ergocalciferol), dl-α-tocopherol, dl-tocopherol, 2-L-ascorbic acid diester potassium, acetic acid dl-α-tocopherol, pantothenic acid and biotin; hormones such as estradiol and ethinyl estradiol; amino acids such as arginine, aspartic acid, cystine, cysteine, methionine, serine, leucine and tryptophan; anti-inflammatory agents such as allantoin, glycyrrhethinic acid and azulene; whitening agents such as arbutin; astringents such as zinc oxide and tannic acid; refrigerants such as L-menthol and camphor; sulfur; lysozyme chloride; pyridoxine chloride; and γ-oryzanol. Also, the above medicaments can be used in a free state; those capable of salt formation can be used not only in a free state but also in the form of a salt of an acid or a base if the medicament is of the salt-making type. On the other hand, the medicaments having a carboxylic acid group can be used in the form of an ester.

The cosmetics of the present invention can contain, as required, any suitable perfumes, colorants and the like unless the objects and the effects (dispersibility, dispersion stability and the like) of the present invention are impaired.

The agent form of the cosmetics of the present invention is not particularly limited. As the agent form of the cosmetics, a heretofore known agent form (type) such as the form of a bi-layer type, a three-layer type, a water in oil (W/O) emulsion, an oil in water (O/W) emulsion, a gel, a spray, a mousse, oil, solid or a stick can be selected. As the agent form of the cosmetics of the present invention, the form of the bi-layer type, the three-layer type, the water in oil (W/O) emulsion, the oil in water (O/W) emulsion, the gel, the spray, the mousse, the oil, the solid or the stick is preferably selected. Especially for use in a sunscreen agent, the form of the bi-layer, the W/O emulsion or the gel is preferably selected, and for use in a foundation, the form of the solid, the solid emulsion, the gel, the W/O emulsion, the O/W emulsion, the oil or the mousse is preferably selected. Specific examples thereof include a skin care essence, an under-makeup gel, a foundation such as a gel foundation, a hair styling gel, a body gel, a massage gel, a pack such as a jelly pack, an emulsion, a cream, a beauty liquid, a hair dressing agent, a hair cream, a hair rinse, a hair dye, a hair mascara, a sunscreen gel, a moisture gel, a sunscreen lotion, a suncum lotion, a lipstick, a nail color, an eye liner and the like. As the specific form of the cosmetics in the present invention, a jelly pack, a gel foundation, a suncum lotion or an emulsion is especially selected. When such forms are selected, the cosmetics are excellent not only in ease of re-dispersion, dispersion stability with lapse of time and a moist touch but also in other effects. Specifically, when the jelly pack is selected as the agent form, it is also excellent in effect of extension (spreadability) on skin. When the gel foundation is selected, it is excellent in adhesion to skin and also effect of long wear. When the suncum lotion is selected, an effect of extension (spreadability) on skin is good, a moist touch is imparted to the skin, and a refreshed (cool) feeling is also provided. When the emulsion is selected, affinity for skin (absorption feeling to the skin) is good, effects of tonicity and elasticity of skin are excellent, drab is improved, and a transparent feeling of skin is excellent.

This application is based on the Japanese Patent Application Serial No. 2004-057674, filed on March 2, 2004, which is incorporated herein by reference in its entirety.

EXAMPLES

The present invention is illustrated more specifically below by referring to Examples. However, the present invention is not limited thereto.

Producing Example 1

Production (Preparation) of Hydrophilicaly Treated Silicone Resin-1

2.5 g of o-[2-hydroxy-3-(trimethylammonio)propyl]hydroxyethylcellulose chloride was added to 200 g of purified water, and uniformly dissolved therein. To the resulting solution were added 200 g of a 1% aqueous solution of monomethylsilanetriol lactate and 57 g of polymethylsilsesquioxane (tradename: TOSPEARL145A, manufactured by Toshiba Silicones, Ltd.) as a silicone resin, and the mixture obtained was treated with a ball mill for 16 hours. After the treatment, the resulting slurry was taken out, washed with water, filtered and cleansed (washed). Subsequently, the thus-obtained mixture was dried, and then pulverized to obtain desired silicone resin with the surface hydrophilicaly treated.

Producing Example 2

Production of Hydrophilicaly Treated Silicone Resin-2

0.5 g of o-[2-hydroxy-3-(trimethylammonio)propyl] chloride guar gum was dissolved in 730 g of purified water. 6.5 g of polydimethylmethylenepiperidinium chloride and 1 g of methylsilanol-tri-PEG-8-glyceryl cocoate were added to the resulting solution, and uniformly dissolved therein.

73 g of polymethylsilsesquioxane (trade name: TOSPEARL 120A, manufactured by Toshiba Silicones, Ltd.) as a silicone resin was added to the thus-obtained solution, and the obtained mixture was maintained at 50° C., and stirred for 10 hours, followed by cooling. Subsequently, the resulting slurry was taken out, washed with water, filtered, and cleansed. The thus-obtained mixture was dried, and then pulverized to obtain desired silicone resin with the surface hydrophilicaly treated.

Producing Example 3

Production of Hydrophilicaly Treated Silicone Resin-3

2.0 g of o-[2-hydroxy-3-(trimethylammonio)propyl]hydroxyethylcellulose chloride was added to 400 g of purified water, and uniformly dissolved therein. 2.0 g of monomethylsilanetriol bound to a hydroxyl group of a resinous polyol ester and 1.0 g of a methacryloylethyldimethylbetaine-2-hydroxyethyl methacrylate copolymer were added to the resulting solution, and uniformly dissolved therein. To the thus-obtained solution was added 73 g of polymethylsilsesquioxane (trade name: TOSPEARL 2000B, manufactured by Toshiba Silicones, Ltd.) as a silicone resin, and the mixture obtained was stirred at 60° C. for 18 hours. The reaction mixture obtained was then cooled, and the resulting slurry was taken out, washed with water, filtered, and cleansed. Subsequently, the thus-obtained mixture was dried, and then pulverized to obtain desired silicone resin with the surface hydrophilicaly treated.

Evaluation Example 1

The respective samples were evaluated by the following evaluation method. As the samples, the hydrophilicaly treated (surface-treated) silicone resins obtained in the above Producing Examples 1 to 3 and untreated silicone resin were used.

(Evaluation Method)

Accurately 32 g of purified water was charged into a transparent vessel having a capacity of 70 ml. 1.0 g of the sample was added thereto, strongly filtered 40 times each day, and then allowed to stand still to evaluate the dispersed state at that time. The same procedure was repeated, and it was evaluated whether the powder was gathered (how many times the sample was strongly shaken to gather the silicone resin (particles)) in the gas-liquid interface.

(Evaluation Results)

As a result, although any of the surface-treated silicone resins obtained in Producing Examples 1, 2 and 3 was strongly shaken 1,000 times, it was clearly dispersed, and a change such as gathering of particles (aggregation (agglomeration) of particles) in the gas-liquid interface was not observed at all. Meanwhile, in all of the untreated silicone resin, the particles were gathered in the gas-liquid interface.

Since the untreated silicone resin was not dispersed, purified water as a dispersion medium was transparent.

Evaluation Example 2

The respective samples were evaluated by the following evaluation method. As the samples, the surface-treated silicone resins obtained in Producing Examples 1, 2, and 3 were only used among the samples used in the above Evaluation Example 1.

(Evaluation Method)

Each of the samples was allowed to stand still at ordinary temperature for 2 years, at 40° C. for 3 months, and at 50° C. for 2 months, and the conditions at each time were observed. Further, after the observation, it was evaluated whether the sample was clearly re-dispersed or not, when the transparent vessel was shaken twice (on ease of re-dispersion).

(Evaluation Results)

As a result, an abnormal change such as gathering of particles or agglomeration of particles in the gas-liquid interface was not observed at all in the samples, which were allowed to stand still under the respective conditions. Also in the evaluation of the ease of re-dispersion, the samples were clearly re-dispersed, and the abnormal change such as gathering of particles or the like in the gas-liquid interface was not observed at all after allowing the samples to stand still.

Example 1

Preparation (Production) of Cosmetic-1

A cosmetic (hair mascara) was prepared (produced) according to the following method based on the composition of the following Table 1.

(Preparation Method)

Components (1), (2) and (11) were dispersed in component (15). Then, a mixture obtained by previously mixing component (10) with component (12) was added to the resulting dispersion. Components (5) and (6) were added to the resulting mixture, and components (3), (4), (7), (8), (9), (13) and (14) were further added thereto, and were mixed with stirring, to obtain a desired cosmetic.

It is preferable that components (4), (8) and (14) are previously swollen in water.

TABLE 1

Composition of a cosmetic (hair mascara) (unit: parts by weight)

| | Components | Amount |
|---|---|---|
| (1) | iron oxide | 4.5 |
| (2) | ultramarine | 0.5 |
| (3) | iridescent pigment | 5.0 |
| (4) | bentonite | 3.0 |
| (5) | silica fine powder* | 1.0 |
| (6) | hydrophilicaly treated silicone resin obtained in Producing Example 1 | 2.0 |
| (7) | polyethylene glycol 400 | 10.0 |
| (8) | xanthane gum | 1.0 |
| (9) | alkyl acrylate copolymer emulsion | 10.0 |
| (10) | brucine-modified alcohol (95%) | 10.0 |
| (11) | sodium hexametaphosphate | 0.1 |
| (12) | methylparaben | 0.3 |
| (13) | perfume | 0.05 |
| (14) | carboxymethylcellulose | 0.05 |
| (15) | purified water | balance |

*Aerosil 200

Comparative Example 1

Preparation of Cosmetic-2

A cosmetic (hair mascara) was prepared in the same manner as in Example 1 except that 2.0 parts by weight of purified water was used instead of hydrophilicaly treated silicone resin obtained in Producing Example 1.

Example 2

Preparation of Cosmetic-3

A cosmetic (gel foundation) was prepared according to the following method based on the composition of the following Table 2.

(Preparation Method)

Components (6) to (11) were dispersed and dissolved in component (16). Components (1) to (5) were dispersed in the resulting mixture. Further, the other components (components (12) to (15)) were added to the resulting dispersion, and were mixed with stirring to obtain a desired cosmetic.

TABLE 2

Composition of a Cosmetic (gel foundation) (unit: parts by weight)

| | Components | Amount |
|---|---|---|
| (1) | talc | 4.0 |
| (2) | titanium dioxide | 5.0 |
| (3) | iron oxide | 0.6 |
| (4) | hydrated iron oxide | 1.0 |
| (5) | tri-iron tetroxide | 0.1 |
| (6) | bentonite | 1.5 |
| (7) | silica fine powder* | 0.5 |
| (8) | hydrophilicaly treated silicone resin obtained in Producing Example 2 | 3.0 |
| (9) | 1,2-pentanediol | 1.0 |
| (10) | 1,3-butylene glycol | 5.0 |
| (11) | xanthane gum | 0.5 |
| (12) | polyethyl acrylate ester emulsion | 1.0 |
| (13) | aqueous ammonia | 0.01 |
| (14) | methylparaben | 0.01 |
| (15) | perfume | 0.05 |
| (16) | purified water | balance |

*Aerosil 200

Comparative Example 2

Preparation of Cosmetic-4

A cosmetic (gel foundation) was prepared in the same manner as in Example 2 except that 3.0 parts by weight of purified water was used instead of the hydrophilicaly treated silicone resin obtained in Producing Example 2.

Example 3

Preparation of Cosmetic-5

A cosmetic (jelly pack) was prepared according to the following method based on the composition of the following Table 3.

(Preparation Method)

Components (2) to (6) were added to component (1), and subsequently, the mixture obtained, was heated. Component (7) was added to the mixture obtained, to prepare a uniform solution. Component (8) was added to the resulting mixed solution, and dispersed therein. Further, a mixture obtained by previously dissolving components (10) to (13) in component (9) and a mixture obtained by previously dissolving component (14) in component (15) were added to the mixture (dispersion) obtained, and mixed therewith. Next, the resulting mixture was de-aerated, and cooled to obtain a desired cosmetic.

TABLE 3

Composition of a Cosmetic (jelly pack) (unit: parts by weight)

| | Components | Amount |
|---|---|---|
| (1) | purified water | balance |
| (2) | glycerin | 1.5 |
| (3) | 1,2-pentanediol | 1.0 |
| (4) | 1,3-butylene glycol | 1.5 |
| (5) | polyethylene glycol | 1.0 |
| (6) | polyoxypropylene (20) methylglycoside | 3.0 |
| (7) | polyvinyl alcohol | 13.5 |
| (8) | hydrophilicaly treated silicone resin obtained in Producing Example 3 | 10.0 |
| (9) | ethanol | 5.0 |
| (10) | methylparaben | 0.1 |
| (11) | perfume | 0.1 |
| (12) | polyoxyethylene (20) polyoxypropylene glycol (20) | 1.5 |
| (13) | polyoxypropylene (9) diglyceryl ether | 2.0 |
| (14) | epsilon-aminocaproic acid | 0.2 |
| (15) | purified water | 0.9 |

Comparative Example 3

Preparation of Cosmetic-6

A cosmetic (jelly pack) was prepared in the same manner as in Example 3 except that 10.0 parts by weight of untreated silicone resin was used instead of hydrophilicaly treated silicone resin obtained in Producing Example 3.

Example 4

Preparation of Cosmetic-7

A cosmetic (suncum lotion) was prepared according to the following method based on the composition of the following Table 4.

(Preparation Method)

Components (2), (3) and (4) were added to component (1), and uniformly dissolved therein. Then, components (5) to (10) were added to the mixture obtained, and uniformly dispersed therein. Further, an ethanol solution obtained by previously dissolving components (11) and (13) in component (12) was added to the resulting dispersion, and the mixture obtained was stirred. Subsequently, components (15) and (16) were added to the mixture obtained, and mixed therewith with stirring, to obtain a desired cosmetic.

TABLE 4

Composition of a cosmetic (suncum lotion) (unit: parts by weight)

| | Components | Amount |
|---|---|---|
| (1) | purified water | balance |
| (2) | glycerin | 5.0 |
| (3) | sodium chloride | 0.2 |
| (4) | epsilon-aminocaproic acid | 0.5 |
| (5) | bentonite | 0.2 |
| (6) | hydrophilicaly treated silicone resin obtained in Producing Example 1 | 2.5 |
| (7) | hydrophilicaly treated silicone resin obtained in Producing Example 3 | 2.5 |
| (8) | talc | 0.5 |
| (9) | zinc oxide | 0.6 |
| (10) | sericite | 0.5 |
| (11) | oxybenzon | 0.05 |
| (12) | ethanol | 7.0 |
| (13) | methylparaben | 0.2 |
| (14) | perfume | 0.2 |
| (15) | sorbitol | 1.0 |
| (16) | polyethylene glycol | 0.5 |

Comparative Example 4

Preparation of Cosmetic-8

A cosmetic (suncum lotion) was prepared in the same manner as in Example 4 except that 2.5 parts by weight of purified water was used instead of hydrophilicaly treated silicone resin obtained in Producing Example 1 and 2.5 parts by weight of purified water instead of hydrophilicaly treated silicone resin obtained in Producing Example 3.

Example 5

Preparation of Cosmetic-9

A cosmetic (emulsion) was prepared according to the following method based on the composition of the following Table 5.

(Preparation Method)

Components (1) to (5), (7) and (8) were dissolved through heating, and then mixed to prepare an oil phase component, and the resulting oil phase component was maintained at 80° C. Meanwhile, components (8) to (15) were dissolved in component (18), and subsequently, components (16) and (17) were further added to the mixture obtained, and uniformly dispersed therein. The resulting mixture was maintained at 80° C. to form an aqueous (water) phase component. The above aqueous phase component was added to the above oil phase component for emulsification. After the emulsion was cooled, component (6) was added to the emulsion to obtain a desired cosmetic. Also, the appearance of the resulting cosmetic was semi-transparent.

TABLE 5

Composition of a cosmetic (emulsion) (unit: parts by weight)

| | Components | Amount |
|---|---|---|
| (1) | squalane | 1.0 |
| (2) | diethoxyethyl succinate | 8.0 |
| (3) | glyceryl tri-2-ethylhexanoate | 1.0 |
| (4) | cetyl isooctanoate | 1.0 |
| (5) | octamethylcyclotetrasiloxane | 1.0 |
| (6) | perfume | 0.2 |
| (7) | butylparaben | 0.2 |
| (8) | 1,3-butylene glycol | 4.5 |

TABLE 5-continued

Composition of a cosmetic (emulsion) (unit: parts by weight)

| | Components | Amount |
|---|---|---|
| (9) | ethanol | 3.0 |
| (10) | alkyl-modified carboxyvinyl polymer | 0.2 |
| (11) | potassium hydroxide | 0.1 |
| (12) | corn starch | 2.5 |
| (13) | L-arginine L-aspartate | 0.01 |
| (14) | succinic acid | 0.01 |
| (15) | sodium succinate | 0.09 |
| (16) | hydrophilicaly treated silicone resin obtained in Producing Example 2 | 1.0 |
| (17) | hydrophilicaly treated silicone resin obtained in Producing Example 3 | 2.0 |
| (18) | purified water | balance |

Comparative Example 5

Preparation of Cosmetic-10

A cosmetic (emulsion) was prepared in the same manner as in Example 5 except that 1.0 part by weight of purified water was used instead of hydrophilicaly treated silicone resin obtained in Producing Example 2 and 2.0 parts by weight of purified water instead of hydrophilicaly treated silicone resin obtained in Producing Example 3. Furthermore, the appearance of the resulting cosmetic was white.

Example 6

Comparative Evaluation of the Cosmetics Obtained in Examples and the Cosmetics Obtained in Comparative Examples The cosmetics obtained in Examples and Comparative Examples described above were evaluated.

(Evaluation Methods and Evaluation Results)

(1) Jelly Pack

In the cosmetic of the present invention (jelly pack obtained in Example 3), hydrophilicaly treated silicone resin (particles) was dispersed quite well, and smoothly extended during application. The persistence of the dispersion effect was good, and the cosmetic was stable after 2 months at 50° C. With respect to the smooth feeling, the moist touch of skin was considerably provided after peeling the film. Meanwhile, in the jelly pack obtained in Comparative Example 3, silicone resin (particles) was agglomerated (aggregated), and not uniformly dispersed. Consequently, a rough feeling was given to the skin in applying thereon. An uncomfortable feeling was imparted much to the skin, or non-uniformity of the applied film (makeup film) was clearly observed.

(2) Gel Foundation

In the cosmetic of the present invention (gel foundation obtained in Example 2), the state of the sample after storage at 40° C. for 3 months was evaluated by visual observation. Consequently, the stability with lapse of time was excellent. Also in the results of observation with an optical microscope, the dispersed state thereof was good. With respect to the smooth feeling, a new touch was provided with a residual moist touch despite a cool feeling. Regarding long wear, the touch immediately after application was maintained, and the uniform makeup film was provided with a natural finish. Meanwhile, in the gel foundation obtained in Comparative Example 2, the propensity of agglomeration of pigments (talc, titanium dioxide, iron oxide and tri-iron tetroxide) was notably observed. As a result, particles agglomerated by an external force in application on the skin were dispersed in the agglomerated state, so that a clear difference in hue (color phase) was observed between appearance color and application color.

(3) Suncum Lotion

In the cosmetic of the present invention (suncum lotion obtained in Example 4), the dispersed state of the pigments (talc, zinc oxide, sericite, and bentonite) was quite good, and the pigments were easily (readily) re-dispersed by shaking upon use. In the observation with lapse of time at 40° C. for 3 months, the precipitation rate and the precipitation volume of the powder (pigments (talc, zinc oxide, sericite and bentonite) were approximately the same as the values of standard characteristics. With regard to touch, there was no slimy felling, and the draw rate and the draw intention were appropriate. With respect to smooth feeling after application, there was no tackiness, and a moist touch and a cool feeling were also good. Meanwhile, with regard to the suncum lotion obtained in Comparative Example 4, the pigments were liable to be agglomerated therein, and a rough feeling was therefore given. Thus, the feeling was bad. In the observation with lapse of time at 40° C. for 3 months, the pH was liable to decrease, or the re-dispersion was difficult even by shaking. The precipitation volume of the powder was liable to be uneven, and the stability with lapse of time was also deteriorated.

(4) Emulsion

In the cosmetic of the present invention (emulsion obtained in Example 5), the dispersed state of hydrophilicaly treated silicone resin (particles) and hydrophilicaly treated silicone resin (particles) was good. The fineness was unchanged over the course of time at temperatures of 20° C., 40° C., 5° C. and 0° C. The application feeling was light and soft, with a smooth feeling on the skin. With respect to the feeling after application, the affinity for the skin, the smoothness of the skin, and a moist feeling on the skin, without any feeling of tackiness were given, and the whiteness of the powder itself was not noticeable. With regard to the cosmetic of the present invention, a test of long-term and continuous use (application) for 3 months was conducted, and the condition (form) of the surface of the skin was then observed by a tape stripping method. Consequently, the skin plateau was plump and raised. This condition was clearly different from the condition before use, and tonicity, elasticity, drab, and transparency of the skin were improved. Meanwhile, in the emulsion obtained in Comparative Example 5, the agglomerated particles of silicone resin and polystyrene were much observed. Consequently, the rough feeling was provided, and both the smooth feeling and the smooth feeling after application were bad.

(5) Hair Mascara

In the cosmetics of the present invention (hair mascaras obtained in Examples 1), the dispersed state of hydrophilicaly treated silicone resin was good, and the change with lapse of time thereof was not observed under each conditions of 0° C., 5° C., 10° C., 20° C., 40° C. and an aging condition 0 to 40° C. The dispersed state of the pigments (iron oxide, ultramarine, iridescent pigment and bentonite) was good without tackiness, the adhesion to the skin was even, and a feeling of dewy, moist touch with a smooth spread were provided. Meanwhile, in the hair mascara obtained in Comparative Example 1, the pigments were liable to be agglomerated. As a result, a rough feeling occurred, and the feeling was bad.

It should be noted that other objects, features and aspects of the present invention will become apparent in the entire disclosure and that modifications may be done without departing the gist and scope of the present invention as disclosed herein and claimed as appended herewith. Also it should be noted that any combination of the disclosed and/or claimed elements, matters and/or items may fall under the modifications aforementioned.

What is claimed is:

1. A powder for a cosmetic comprising surface-treated silicone resin particles which are hydrophilic wherein said silicone resin particles are polymethylsilsesquioxane,
wherein the surface treatment is a coating with at least one of dimethylsilanediol hyaluronate, monomethylsilanetriol lactate, methylsilanol-tri-PEG-8-glyceryl cocoate, monomethylsilanetriol mannuronate and elastin peptide silane and a water-soluble cationic polymer.

2. The powder as claimed in claim 1, wherein the silicone resin particles prior to surface treatment have a mean particle size of from 0.1 to 100 μm.

3. The powder as claimed in claim 1, wherein said coating is from 0.1 to 50% by weight, based on the silicone resin particles prior to surface treatment.

4. The powder as claimed in claim 1, wherein said water-soluble cationic polymer is at least one water-soluble cationic polymer selected from the group consisting of a dimethyldiallylammonium chloride-acrylamide copolymer, polydimethylmethylenepiperidinium chloride and o-[2-hydroxy-3-(trimethylammonio)propyl]hydroxyethylcellulose chloride.

5. A dispersion for a cosmetic which comprises the powder of claims 1, 2, 3, and 4.

6. A cosmetic which comprises the powder of claims 1, 2, 3, and 4.

7. The cosmetic as claimed in claim 6, wherein said powder is comprised from 0.1 to 99% by weight based on the total composition of the cosmetic.

8. The cosmetic as claimed in claim 6, wherein said cosmetic is a bi-layer cosmetic, a three-layer cosmetic, a water-in-oil emulsion, an oil-in-water emulsion, a gel, a spray, a mousse, an oil, a solid or a stick.

9. The cosmetic as claimed in claim 6, which is a jelly pack, a gel foundation, a suncalm lotion or an emulsion.

* * * * *